United States Patent
Okkels (10) Patent No.: US 9,599,548 B2
(45) Date of Patent: Mar. 21, 2017

(54) FLOW MEASUREMENT DEVICE AND METHOD

(75) Inventor: Fridolin Okkels, Copenhagen S (DK)

(73) Assignee: Danmarks Tekniske Universitet, Lyngby (DK)

( * ) Notice: Subject to any disclaimer, the term of this patent is extended or adjusted under 35 U.S.C. 154(b) by 602 days.

(21) Appl. No.: 14/123,827

(22) PCT Filed: Jun. 22, 2012

(86) PCT No.: PCT/DK2012/050210
§ 371 (c)(1),
(2), (4) Date: Feb. 6, 2014

(87) PCT Pub. No.: WO2012/175093
PCT Pub. Date: Dec. 27, 2012

(65) Prior Publication Data
US 2014/0137640 A1  May 22, 2014

Related U.S. Application Data

(60) Provisional application No. 61/499,845, filed on Jun. 22, 2011.

(30) Foreign Application Priority Data

Jun. 22, 2011  (EP) ................................ 11171010

(51) Int. Cl.
*G01N 11/08* (2006.01)
*G01F 1/40* (2006.01)

(52) U.S. Cl.
CPC .............. *G01N 11/08* (2013.01); *G01F 1/40* (2013.01)

(58) Field of Classification Search
CPC ..... G01N 11/08; G01L 15/00; G01L 19/0092; G01L 9/0042; G01F 1/40
See application file for complete search history.

(56) References Cited

U.S. PATENT DOCUMENTS 4,831,869 A * 5/1989 Fowler ................... G01N 13/00
   73/150 A
6,386,016 B1 * 5/2002 Gleissle ................. G01N 11/08
   73/54.01

(Continued)

FOREIGN PATENT DOCUMENTS

CN     1610823 A   4/2005
CN   101124467 A   2/2008

(Continued)

OTHER PUBLICATIONS

Bandey et al., "Blood rheological characterization using the thickness-shear mode resonator," Biosensors and Bioelectronics, 19:1657-1665 (2004).

(Continued)

*Primary Examiner* — Daniel S Larkin
*Assistant Examiner* — Jamar Ray
(74) *Attorney, Agent, or Firm* — Knobbe Martens Olson & Bear LLP (57) ABSTRACT

The present invention relates to a fluid measuring device comprising a capillary device and a non-linear response device. The capillary device typically having a flow channel comprising a contraction with a sidelet upstream and sidelet downstream of the contraction, the sidelets each comprises a pressure sensor arranged to determine the pressure drop over the contraction, the geometry of the flow channel of the capillary device being adapted to provide a flow response by the linear effects in the fluid, with the least response from the non-linear effects in the fluid. The non-linear response device typically having a flow channel connected to the flow channel of the capillary device, the flow channel of the non-linear response device comprising sidelets arranged to determine a pressure drop over at least a part of the flow channel, wherein the geometry of the flow channel of the non-linear response device being adapted to provide a flow response primarily driven by the non-linear effects in the fluid.

33 Claims, 6 Drawing Sheets

(56) References Cited

U.S. PATENT DOCUMENTS

| | | | |
|---|---|---|---|
| 6,601,460 B1* | 8/2003 | Materna | G01F 1/40 |
| | | | 73/861.52 |
| 7,059,176 B2* | 6/2006 | Sparks | G01F 1/8404 |
| | | | 73/54.01 |
| 7,770,436 B2 | 8/2010 | Baek | |
| 2003/0079547 A1* | 5/2003 | Baek | G01L 9/0042 |
| | | | 73/716 |
| 2005/0210964 A1* | 9/2005 | Baek | G01L 9/0042 |
| | | | 73/54.28 |

FOREIGN PATENT DOCUMENTS

| | | |
|---|---|---|
| DE | 198 48 687 A1 | 4/2000 |
| WO | WO 03/038388 | 5/2003 |
| WO | WO 2005/086883 | 9/2005 |
| WO | WO 2009/061943 | 5/2009 |

OTHER PUBLICATIONS

Barnes, "Thixotropy—a review," J. Non-Newtonian Fluid Mech., 70:1-33 (1997).

Clasen et al., "Gap-Dependent Microrheometry of Complex Liquids," J. Non-Newtonian Fluid Mech., 124:1-10 (2004).

Waigh, "Microrheology of complex fluids," Rep. Prog. Phys. 68:685-742 (2005).

* cited by examiner

FLOW MEASUREMENT DEVICE AND METHOD

CROSS REFERENCE TO RELATED APPLICATIONS

This application is a U.S. National Phase Application of PCT International Application Number PCT/DK2012/050210, filed on Jun. 22, 2012, designating the United States of America and published in the English language, which is an International Application of and claims the benefit of priority to European Patent Application No. 11171010.9, filed on Jun. 22, 2011, and U.S. Provisional Application No. 61/499,845, filed on Jun. 22, 2011. The disclosures of the above-referenced applications are hereby expressly incorporated by reference in their entireties.

FIELD OF THE INVENTION

The present invention relates to a fluid measuring device comprising a capillary device and a non-linear response device. The capillary device typically having a flow channel comprising a contraction with a sidelet upstream and sidelet downstream of the contraction, the sidelets each comprises a pressure sensor arranged to determine the pressure drop over the contraction, the geometry of the flow channel of the capillary device being adapted to provide a flow response by the linear effects in the fluid, with the least response from the non-linear effects in the fluid. The non-linear response device typically having a flow channel connected to the flow channel of the capillary device, the flow channel of the non-linear response device comprising sidelets arranged to determine a pressure drop over at least a part of the flow channel, wherein the geometry of the flow channel of the non-linear response device being adapted to provide a flow response primarily driven by the non-linear effects in the fluid.

The invention also relates to method of utilising devices according to the present invention.

BACKGROUND OF THE INVENTION

Reference is made to WO 2009/061943 A9, Publication 14 May 2009 Entitled: Micro Rheometer for measuring flow viscosity and elasticity for micro sample volumes, and Helen L. Bandey et al. (Helen et al), Blood rheological characterization using the thickness-shear mode resonator, Biosensors and Bioelectronics 19, 1657 (2004).
Choice of Materials The device described in WO 2009/061943 A9 involves electrodes of Au (gold), and it is therefore very sensitive to high temperatures. The devices disclosed in WO 2009/061943 A9 are explicitly described as being fabricated using clean-room techniques, which involve less corrosion and heat-resistive metals.
Mobility and Robustness Against Varying Working Conditions Even though the fluid characterization in both WO 2009/061943 A9 and Helen et al involves small microchannel, these two devices, as described in WO 2009/061943 A9 and Helen et al., cannot be realized in a mobile handheld device of the same dimensions and weight as for the invention (described above), because they both depend on a pump producing a fixed precise volume-flowrate. With present prior art technology, such pumps must be syringe-pumps, which exceeds more than 10 fold the volume and weight of the invention, as described above.

Further Drawback

The devices and methods disclosed in WO 2009/061943 A9 and Helen et al also suffer the draw back of being less efficient, difficult to produce and sensitive to external influences.

OBJECT OF THE INVENTION

Hence, improved devices and methods for determining one or more properties of fluid would be advantageous, and in particular a more efficient and/or reliable device and method would be advantageous.

It is a further object of the present invention to provide an alternative to the prior art.

In particular, it may be seen as an object of the present invention to provide a device and a method that solves the above mentioned problems of the prior art.

SUMMARY OF THE INVENTION

Thus, the above described object and several other objects are intended to be obtained in a first aspect of the invention by providing a fluid measuring device preferably comprising a first device herein referred to as a capillary device and a second device herein referred to as a non-linear response device wherein
  the capillary device having a flow channel comprising a contraction with a sidelet upstream and sidelet downstream of the contraction, the sidelets each comprises a pressure sensor arranged to determine the pressure drop over the contraction, the geometry of the flow channel of the capillary device being adapted to provide a flow response by the linear effects in the fluid, with the least response from the non-linear effects in the fluid,
  the non-linear response device having a flow channel connected, preferably directly, to the flow channel of the capillary device, the flow channel of the non-linear response device comprising sidelets arranged to determine a pressure drop over at least a part of the flow channel, wherein the geometry of the flow channel of the non-linear response device being adapted to provide a flow response primarily driven by the non-linear effects in the fluid.

Preferably, a fluid measuring device according to the present invention may comprise a capillary device and a non-linear response device wherein
  the capillary device comprising a flow channel for determining the volume flow through the channel and two sidelets each comprising a pressure sensor arranged at a distal end of the sidelet, the sidelets being arranged in the capillary device to determine the pressure drop over at least a part of flow channel,
  the non-linear response device comprising a flow channel directly connected to the flow channel of the capillary device, the flow channel of the non-linear response device being a curved channel and comprising sidelets each comprising a pressure sensor arranged at distal end of the sidelet, the sidelets being arranged to determine a pressure drop over at least a part of the flow channel, the curved channel comprising
    two opposite curved wall sections extending asymmetrically to each other at least through out a part of the flow channel, wherein
      one of the opposing curved wall sections defines a bump in the flow channel,
    an opening of one of the sidelets arranged immediately downstream of maximum height of the bump.

Preferably, the geometry of the flow channel of the capillary device being adapted to provide a flow response by the linear effects in a fluid, with the least response from the non-linear effects in the fluid.

Preferably, two opposite curved wall sections extends asymmetrically to each other at least through out a part of the flow channel so as to provide a fluid deflection into a flow pattern with curved stream lines from an inlet and to an outlet of the flow channel with increased shear in flow regions at the bump First, the invention differs from a broad group of rheometers (e.g. conventional cup-rheometers) as the invention does not involve movement of any other material than the fluid to be investigated. Second, the invention does not require any additives to be added to the fluid as part of the measurement procedure.

The action of the invention involves primarily the creation of specific flow patterns, arising from the contact between the fluid and a spatial structuring of the channel-walls. Therefore, a preferred constraint on the channel-wall material is that it should be rigid. On that basis, highly resistant channel-wall materials can be chosen, such that the invention can characterize fluids, which can be very reactive and corrosive. Similarly, channel-wall materials can be chosen (e.g. ceramics), such that the invention can characterize fluid-gasses at high temperature (e.g. above the melting temperature of most metals used in the chemical industry, that is 1500° C.).

The physical dimensions of the invention can then be reduced dramatically, compared to common cup-rheometers, without compromising the functionality. This is partly because the invention does not involve any moving parts, except of the fluid, and also because the physical phenomena, utilized in the functionality of the invention, does not require large volumes of the fluid. This, combined with the fact that the energy consumption required for operating the invention is small enough to be supplied by a small battery, makes it possible for one realization of the invention to be a handheld device.

Preferably, the curved wall section opposing the curved wall section defining a bump extends in a manner increasing or decreasing the cross sectional area of the flow channel downstream of the bump.

In preferred embodiments of the fluid measuring device according to the invention, wherein the flow channel of the linear flow response device is a straight channel.

Preferably, the curved wall section defining a bump extends from the inlet of the non-linear response device and to the top of the bump in a convex manner and in a convex manner from the top of the bump and to the outlet of the non-linear response device, and the opposing wall section extend from the inlet and to the outlet of the non-linear response device in a concave manner.

Furthermore, the sidelets of the non-linear response device are preferably arranged on opposite sides of the flow channel.

In many preferred embodiments of the invention, the capillary device being adapted to produce a symmetric flow inside the flow channel.

Typically, the volume of the flow channel of the non-linear response device is preferably at least 2 times, such as at least 4 times, preferably at least 8 times larger than the volume of the flow channel of the capillary device.

In some preferred embodiments, the flow channels and the sidelets of the measuring device are square-shaped.

According to many preferred embodiments of the invention, the flow channels and sidelets of the measuring device are provided in a single block of material, preferably by cutting, milling, moulding, or electric discharge machining. Furthermore, the flow channels and sidelets of the measuring device are preferably defined by wall elements made of plastic or metal.

In certain preferred embodiments of the invention, the flow channel of the capillary device comprising a narrowing section upstream and a expanding section downstream of a contraction preferably being a straight section, preferably with the sidelets being arranged upstream and downstream of the contraction.

Preferably, the geometrical dimensions of the flow channel of the capillary device, the flow channel of the non-linear response device and of the sidelets is in the micro meter range size.

In many preferred embodiments of the invention, the flow channel of the non-linear response device comprising a constriction at an inlet of the flow channel, and wherein flow channel downstream of the constriction has a diffuser geometry with diverging sides, the diffuser geometry is terminated by a wall having an outlet, a sidelet is arranged at the constriction and a sidelet is arranged at the wall.

In further preferred embodiments, the flow channel of the non-linear response device comprises a single connected transition channel reaching from an inlet to an outlet, and one of the sidelets is connected to the part of transition channel in vicinity of the inlet, and the other of the sidelets is connected to the transition channel in vicinity of outlet, but not in direct connection with the outlet. A substantial geometrical feature, preferably being the parts defining the flow, of the transition channel may preferably consists of two curved walls on opposite sides of the channel, which acts to deflect the fluid flow into a curved path.

Preferred embodiments of the invention may further comprise a pump for pumping fluid through the capillary device and the non-linear response device. Preferably, the pump is a manually actuated pump, such as a piston pump. Furthermore, the measuring device and the pump may advantageously be formed as handheld device in the form of a pipette, such as a micro-pipette.

In preferred embodiments of the invention, the measuring device is integrated in a lab equipments or a production facility.

A particular embodiment, a mobile handheld device, will be small enough to fit within a common micro-pipette, complete with batteries and a small display for showing quantitatively the results from the fluid characterization measurements. There will be no time-delay in processing the measurements into these quantitative results.

For the handheld device the combined dimensions of the following parts: the invention, measurement-processing electronics, battery, and display, is estimated to fit within: 3×1.5×1.5 cm, with a estimated weight below 40 gram.

Furthermore, the manual hand-pump, used on common micro-pipettes, will be sufficient for all fluid transport, since the invention can give precise fluid characterization measurements even in situations where the overall flowrate through the device varies in an uncontrolled manner. This flowrate-correcting functionality makes not only the handheld realizations of the invention, but all realizations very robust against variations in working conditions; this includes also variations in working condition temperature and pressure.

In a second aspect the invention preferably relates to a method of determining one or more properties of a fluid, the method preferably utilizes a device according to the first aspect of the invention, and a characterization of interaction between a given fluid and the channel, the characterization comprising corresponding values of flow rate (Q), or a derived parameter, pressure difference (ΔP) and a property (C) of the fluid. By corresponding values means preferably that they are all obtained for the same flow situation. E.g. for a given flow rate Q' the pressure difference ΔP' is determined and the fluid property C' is known, whereby the corresponding values are [Q', ΔP', C']. The method typically comprising determining the pressure difference over the capillary device and the non-linear response device, and deriving from the characterization the property of the fluid based on the determined pressure differences.

One important effect of the combination of the capillary device used for determining the volume flow and the non-linear response device used for providing the shear-thinning or shear-thickening of the fluid is that the flow through the device needs not to be stationary and/or fully developed. It has e.g. been found that the device works very well with a varying volume flow through the device. In addition, the invention provides the possibility of determining the inherent composition of the fluid, by using the information coming from both the volume flow and the fluid property e.g. a concentration of a substance in the fluid. It is noted that there often exists a relation between pressure difference and flow rate and therefore the flow rate may be expressed as a pressure difference.

Furthermore, as the fluid considered typically is incompressible the flow rate may either be volume flow (such as expressed in m3/h) or mass flow (such as kg/h).

Preferably, a method of determining one or more properties of a fluid according to the present invention utilizes
  a fluid measuring device according to the first aspect of the invention, and
  a characterization of interaction between a given fluid and the flow channel of the fluid measuring device, the characterization comprising corresponding values of a property of the fluid, values of pressure differences between the sidelets of the non-linear response device, and values of either pressure differences between the sidelets of the capillary device ($\Delta P_Q$), flow rates through the device or both
and the method preferably comprises
  feeding a non-Newtonian fluid through the device at a flow rate producing shear-thinning at least locally in the non-linear response device,
  determining the pressure difference between the sidelets of capillary device and of the non-linear response device,
  deriving from the characterization the property of the fluid being fed through the fluid measuring device based on the determined pressure difference between the sidelets of the non-linear device together with the pressure difference between the sidelets of the capillary device.

The non-Newtonian fluid is preferably selected from the group consisting of visco-elastic fluids. Preferably, the fluid is sugar dissolved in water and the property being determined is the sugar concentration, the fluid is paints and the property being determined is the rate of shear-thinning, the fluid is enamel and the property being determined is the rate of shear-thinning, the fluid is engine oil and the property being determined is the degradation of the oil, or the fluid is engine fuel and the property being determined is the type of engine fuel In preferred embodiments, the method further comprises determining to flow rate through the device based on the characterization and the determined pressure differences.

Methods according to preferred embodiments of the invention may further comprise obtaining a characterization by
  feeding a non-Newtonian fluid at number of different known flow rates and with a number of different known properties of the fluid through the device,
  recording the pressure differences between the sidelets of the capillary device and the non-linear response device resulting therefrom
thereby obtaining a characterization comprising corresponding data sets of
  values of flow rates through the device and property of the fluid, and
  pressure differences between the sidelets of the capillary device and the non-linear response device,
for a number of different volume flow rates through the device and for a number of known and different properties of the fluid.

Preferably, the number of different known flow rates is selected between 50 and 100 and the number of different known properties of the fluid is selected between 50 and 100, whereby the number of corresponding data sets is between 2.500 and 10,000.

According to preferred embodiments, the corresponding data sets may be degenerated into corresponding data sets
  of property of the fluid corresponding to the pressure differences between the sidelets of the capillary device and the non-linear response device, or
  of values of the flow rate through the device and property of the fluid corresponding to the pressure differences between the sidelets the non-linear response device,
by use of a functional relations ship between the flow rate and the pressure between the sidelets of the capillary device.

Preferably, the feeding flow rate of the non-Newtonian fluid through the device at a flow rate producing shear-thinning at least locally in the non-linear response device may be constants during the determination of the one ore more properties of the fluid. Alternatively, the feeding flow rate of the non-Newtonian fluid through the device at a flow rate producing shear-thinning at least locally in the non-linear response device may vary during the determination of the one or more fluid properties of the fluid.

The characterization may preferably be stored as a database in electronic storage medium, and the execution of the method may be assisted by use of a computer.

In the present context, a number of terms are used in an ordinary manner. However, for the sake of completeness some of the terms are explained below.

Pressure drop over a channel is preferably used to mean a pressure change being positive or negative in the streamvise direction of the channel Directly connected is preferably use to mean that all the fluid flowing through the capillary device flows through the non-linear response device.

Immediately downstream of the maximum height of the bump is preferably used to mean that the upstream edge of the opening of the sidelet being arranged in a position downstream of the maximum height of the bump being less than 5% such as less than 1% of the distance measured by a straight line extending from the inlet and to the outlet of the non-linear response device.

A bump is preferably used to mean a wall geometry which first tends to increase the boundary layer momentum thickness and subsequently tends to decrease the boundary layer momentum thickness. The maximum height of the bump is preferably used to mean the point (in two dimension) or the line (in three dimension) where the increase in boundary layer momentum thickness changes into a decrease in boundary layer momentum thickness. In many preferred embodiments the maximum height coincides with a geometrical maximum height where the horizontal is direction is defined as the flow direction of the fluid into the device.

A constriction is preferably used to mean that the cross sectional area of a flow channel is locally reduced. A constriction is typically provided by a bump or narrowing cross section in the flow channel. Contraction is preferably used interchangeably with constriction.

Straight channel means preferably a channel extending symmetrically along a straight line; the straight channel may accordingly comprise variations in cross sectional areas.

Herein two realizations of the non-linear response device are introduced with the following names: High shear viscosity device, and Low shear viscosity device.

High shear viscosity device, in short HSV device, means preferably a device in which a flow is established resulting in at least locally shear thinning. Low shear viscosity device, in short LSV device, means preferably a device in which a flow is established in which inertia effects influences the flow. The HSV and LSV devices are members of the generic class of devices named Shear viscosity devices which preferably means a device designed to operated either as a HSV or a LSV device.

The 2 Dimensional Flow Presented is a Representation of a Real Physical 3D Flow

The following embodiments of the invention are presented by flows restricted to two dimensions (2D flow), and this generally corresponds to full three dimensional fluid flows and device structures, where the variation along the third dimension (perpendicular to the presented two dimensions) is insignificant related to the variations along the two presented dimensions. In practice, this can be accomplished by having the height (along the third dimension) of the fluid confinement being at least twice the maximal channel width (along the two presented dimensions).

It is noted that although the present invention as disclosed herein may appear to reside in a 2 dimensional flow regime, the invention is not limited to such 2 dimensional flow regimes. In practice, the invention may operate equally well in a full 3 dimensional flow regime and such regimes are also considered within the scope of the invention.

The devices realizing the invention are preferably based on extruding a planar design into the height dimension, and thereby having a fixed height all over the fluid region. This type of device realization is used since it simplifies the numerical process in obtaining the presented devices, but the invention should not be limited to this planar-based approach, but rather capture any three dimensional channel structure.

Capillary device which preferably is used as an identifying name for a flow device means preferably a device used to determine the volume flow through either the HSV device or the LSC device. As indicated by the wording capillary, the device comprises restricted flow passage(s) but is not restricted to a device producing capillary flow or effects. In general, a capillary is a flow device in which no shear thinning or thickening occur while shear thinning or thickening occur in the non-linear flow device. Similarly a non-linear flow device which preferably is used as an identifying name for a flow device is preferably a device in which shear thinning or thickening occur at the same flow situation which do not create a shear thinning or thickening in the capillary device.

Sidelet means preferably channel branch extending from the flow channel of the flow device and to a pressure sensor constituting a closed end wall of the sidelet. The length of the sidelet is selected so as to be sufficient to assure that substantially no shear is generated by the flow at the closed end wall of the sidelets. In many practical preferred embodiments of the invention, the ratio between the length, L, and the width, W, of the sidelet is typical W/L<0.5 such as W/L<0.25 preferably W/L<0.125 where W is defined as the square root of [cross sectional area of the opening of the sidelet into the flow channel multiplied by 4 and divided by Pi] and the length is defined as the volume of the sidelet divided by the cross sectional area of the opening of the sidelet into the flow channel.

As presented herein, the non-linear response device is in accordance with many preferred embodiments shaped with curved wall section. The curvature of these wall sections are selected so that the effects of curved wall section is to accelerate the fluid to increase the shear in the fluid typically up to a geometrical maxima typically being the maximum height of a bump and subsequently an additional acceleration of fluid. It is noted that "accelerate" is used in the general meaning as a change of local velocity, including situations such as: acceleration, deceleration, and transverse acceleration, where the latter results in a curved flow path. The curvature of the wall sections are preferably designed so that the dot-product between the gradient of the pressure and the velocity inside the channel is close to zero except at a region close to the geometrical maxima.

Shear is used as an abbreviation for shear-rate which in a two dimensional form can be written as (having velocity components u,v in an coordinate system with axis x, y):

$$\dot{\gamma} = \sqrt{2\left(\frac{\partial u}{\partial x}\right)^2 + \left(\frac{\partial u}{\partial y} + \frac{\partial v}{\partial x}\right)^2 + 2\left(\frac{\partial v}{\partial y}\right)^2}$$

It is noted, again, that the invention is not limited to 2 dimensional flow regimes.

Rheometry generically refers to the experimental techniques used to determine the rheological properties of materials, that is the quantitative and qualitative relationships between deformations and stresses and their derivatives.

A flow response by the linear effects means preferably that there exists a significant linear relation between variations in the action (which in this particular case is variations of the flow-rate Q) and the response being measured (which in this particular case is variations of the pressure difference, measured by the pressure sensors at two sidelets).

A flow response by the non-linear effects means preferably that there exists a significant non-linear relation between variations in the action (which in this particular case is variations of the flow-rate Q) and the response being measured (which in this particular case is variations of the pressure difference, measured by the pressure sensors at two sidelets).

A linear relation f(x) is described by a first-order polynomial f(x)=A+B·x, where A, B are real numbers.

A non-linear relation g(x) is a relation which cannot significantly be described by a linear relation. In most cases, a non-linear relation further involves second-order or higher-order polynomials: $g(x)=A+B·x+C·x^2+D·x^3+ \ldots$, where A, B, C, D, . . . are real numbers.

The first, and second aspects of the present invention may each be combined with any of the other aspects. These and other aspects of the invention will be apparent from and elucidated with reference to the embodiments described hereinafter.

BRIEF DESCRIPTION OF THE FIGURES

The various aspects and embodiments according to the invention will now be described in more details with regard to the accompanying figures. The figures show ways of implementing the present invention and are not to be construed as being limiting to other possible embodiments falling within the scope of the invention.

FIG. 5 left hand side part shows a further elaborated version of FIG. 3, where the best shear-thinning (rheological) region is emphasized in transparent grey shading. In FIG. 5 right hand side, the fluid properties on the two curved walls 8a, 8b, indicated by series of symbols, are plotted in the left hand side of FIG. 5 with the same symbols. The lower collection of measurements correspond to a realistic sugar solution as they follow the solid curved, while the upper reference measurements follow a fictitious fluid, where the shear-thinning rate has been artificially lowered. The black double arrow in the left hand part corresponds to the two types of fluid used for designing the LSV device (FIG. 1).

FIG. 7 is an illustration of the first step in the procedure for precisely describing the embodiment of the HSV device. It shows the resulting channel wall geometry arising from the piecewise connected Bezier curves, described by listing the direct control-point coordinates (see table II below). Specific corners of the geometry are marked by red circles, as these corners are to be rounded by a fillet procedure, where a circle of well-defined radii is placed as near to the corners as possible while still touching the two curve-elements tangentially.

DETAILED DESCRIPTION OF THE INVENTION

The present invention resides inter alia in the finding that at least for fluids where the magnitude of internal properties of the fluid such as viscosity depends on the shear of the flow, a device can be designed which can be used to determine properties of the fluid in question. Examples on such devices are presented below.

Low Shear Viscosity Device

Figure 1:
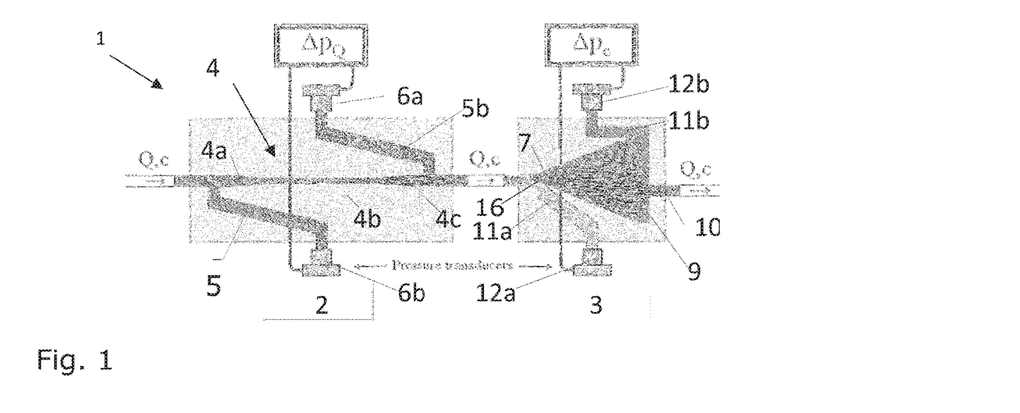
FIG. 1 is a schematic illustration of a preferred embodiment of a measuring device according to the present invention; the embodiment is an example on a low shear viscosity device with an upstream arranged capillary device.

Reference is made to FIG. 1 being a schematic drawing of a preferred embodiment of a measuring device according to the present invention. In FIG. 1 the flow measurement device 1 comprises a capillary device 2 and a non-linear response device 3. The capillary device 2 is a device designed to measure the volume flow going through the downstream non-linear response device by determining the volume flow through the channel of the capillary device (due to fulfillment of the continuity, the volume flow going through the capillary device equals the flow going through the non-linear response device).

The capillary device 2 has an flow channel 4 having a narrowing section 4a—in the form of a funnel—upstream of a contraction 4b, being a straight section, and an expanding section 4c downstream of the contraction 4b. Two sidelets 5a and 5b are connected to the narrowing respectively the expanding section 4a, 4c. The sidelets 5a and 5b are channels communicating the pressure in the fluid in the channel 4 to pressure transducers 6a and 6b respectively. The capillary device 2 is calibrated so that the volume flow Q through the capillary device 2 can be established from the pressure difference detected by the transducers 6a and 6b, that is the volume flow Q is determinable from $\Delta PQ$.

Figure 9:
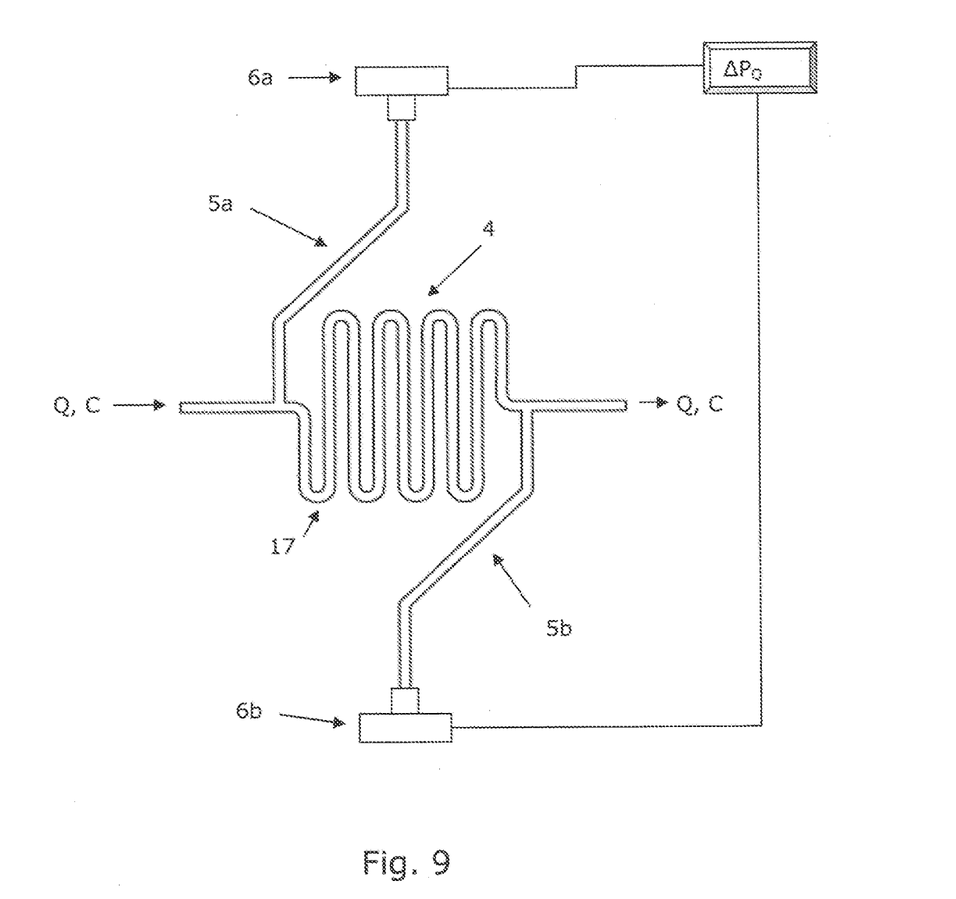
FIG. 9 shows a further embodiment of a capillary device according to preferred embodiments of the present invention

A further embodiment of a capillary device 2 is shown schematically in FIG. 9. In this embodiment, the flow channel 4 has a uniform cross sectional area and comprising a number of bends 17 connecting straight sections of the channel 4. The flow channel 4 can be characterized as an meandering channel. Similarly to the capillary device of FIG. 1, the capillary device of FIG. 9 comprises sidelets 5a, 5b with pressure transducers 6a, 6b arranged at a distal end of a sidelet to determine the pressure difference (pressure drop) over the channel 4.

The non-linear response device 3 is located downstream of the capillary device 2 and receives the same amount of fluid as has passed through the capillary device 2. In the embodiment shown in FIG. 1, the non-linear response device is designed as a low shear viscosity device and comprises a constriction 7 is followed by a diffuser geometry with diverging sides. The constriction 7 formed by a bump (16) in the lower wall of the flow channel. The bump comprising a step with a flat surface facing normal to the incoming flow and a top surface sloping downwardly continuing into the diverging side of the channel. The constriction creates a jet of fluid which spreads out downstream in the diffuser. The diffuser geometry is terminated by a wall 9 having an outlet 10. A sidelet 11a is arranged at the constriction 7 immediately downstream of the maximum height of the bump (16) and a sidelet 11b is arranged at the wall opposite to the wall comprising to bump. This arrangement of sidelets provided a pressure measurement on two opposite sides of the flow through the channel. The sidelets 11a and 11b communicate the pressure in the fluid to pressure transducers 12a and 12b to detect the pressure difference labeled $\Delta P_C$ in FIG. 1.

The device 1 may preferably also comprise a pump to pump (or suck) fluid through device. It is further noted that the channels of the device are closed channels in the sense that they constitute tubes. Furthermore, the capillary device 2 and the non-linear response device 3 are connected without any further elements than the channel leading fluid from the outlet of the capillary device 2 to the inlet of the non-linear response device 3. Often the capillary device 2 and the non-linear response device are formed in a single block of material.

Figure 2A:
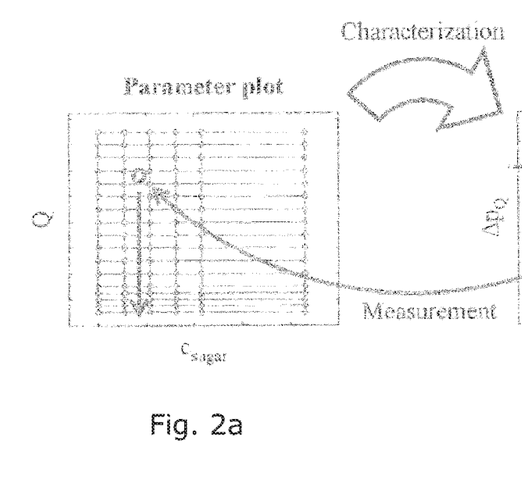
FIG. 2 is an illustration of the procedure for characterizing fluid properties using the LSV device in combination with the capillary device being common to both the LSV and the HSV device. To the left is showed the reference distribution of characterization measurements. The grid at the left plot is then, in the right plot, mapped onto the measurement-space (termed device plot in FIG. 2), spanned by the measured pressure differences from the LSV device and the capillary device, and the arrows indicate the procedure for characterizing the fluid from given measurements.
Figure 2B:
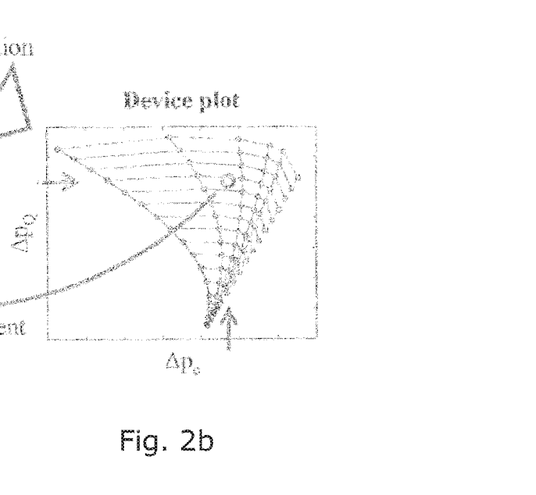
Figure 3:
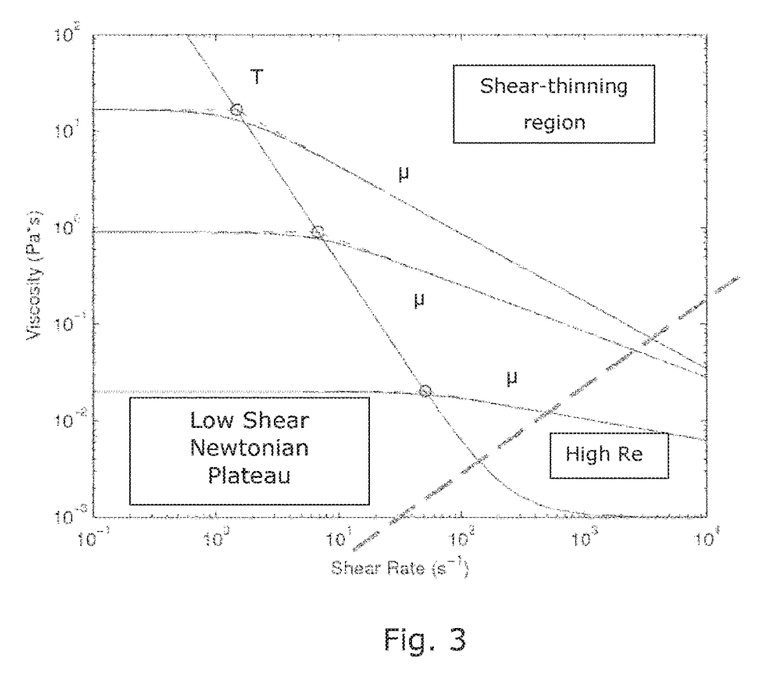
FIG. 3 is a graph illustrating the rheological properties of a sugar solution, as it shows how the logarithm of the solution viscosity depends on the logarithm of the local shear rate. The black curves (labelled $\mu$) show this shear rate dependence for different sugar concentration. The line T shows the general boundary between the Low Shear Newtonian Plateau (LSNP) to the left and the shear-thinning region to the right. The dashed line marks the transition between the low Reynolds number (Re) region to the upper left, and the lower right region of higher Re numbers, where the inertia of the fluid begins to influence the fluid flow.

Reference is made to FIG. 2 illustrating a preferred embodiment of a method according to the present invention. FIG. 2a shows a parameter plot and FIG. 2b shows a device plot. The example considered in FIG. 2 relates to determination of sugar concentration in water. For such a fluid, the magnitude of the viscosity is depended on the shear, if the shear is sufficiently high, and the concentration of sugar (reference is also made to FIG. 3 illustrating the rheological properties of a sugar solution). FIG. 2 illustrates a non-linear mapping between fluid parameters Q, C and measurements $\Delta P_Q$ made by the capillary device to determine the volume flow Q and the measurements made by the non-linear response device 3 to determined the pressure difference $\Delta P_C$.

Before a fluid measuring device 1 according to the present invention is used for determining e.g. sugar concentration of a fluid, a characterization of the device 1 is carried out. The characterization comprises for a number of known and different sugar concentrations, that the volume flow through the non-linear response device 3 is determined by the capillary device 2 and the corresponding pressure difference over the non-linear response device 3 is recorded. Thus, a set of data is produced for each concentration:

| Measurements produced for sugar concentration = x gr/m³ | | |
|---|---|---|
| Volume flow, Q | Pressure difference over capillary device, $\Delta P_Q$ | Pressure difference over non-linear response device, $\Delta P_C$ |
| $Q_1$ | $\Delta P_{Q,1}$ | $\Delta P_{C,1}$ |
| $Q_i$ | $\Delta P_{Q,i}$ | $\Delta P_{C,i}$ |
| $Q_n$ | $\Delta P_{Q,n}$ | $\Delta P_{C,n}$ |

Each such set of data is shown as vertical lines in the $Q, C_{sugar}$ plot of FIG. 2a. This also means that for each data set of $(Q, C_{sugar})$ a corresponding data set of $(\Delta P_Q, \Delta P_C$ is established. In FIG. 2 the corresponding sets of data i.e.

$$(Q, C_{sugar})_{1 \ldots m} <->(\Delta P_Q, \Delta P_C)_{1 \ldots m}$$

has been plotted and their internal correspondence indicated by dots. While the data sets typically are ordered in pairs of data, it should be noted that a corresponding set of data may also include a set of data comprising corresponding values of Q, $C_{sugar}$, $\Delta P_Q$ and $\Delta P_C$.

Upon measuring, that is determination of a unknown sugar concentration in a fluid, the fluid is pumped through the capillary device 2 and through the non-linear response device 3. Corresponding values of $\Delta P'_Q$, $\Delta P'_C$ are determined by the transducers and recorded (a subscript ' is used to indicated measuring an unknown fluid) and the corresponding set of data Q, $C_{sugar}$ is identified whereby both the actual volume flow and the sugar concentration has been determined.

Often there is no exact match in the data sets produced during characterization and an interpolation is therefore carried out. One such interpolation could be based on the four closest set of data as indicated in FIG. 2 where a grid is presented showing cells with corners constituted by pairs of $Q, C_{sugar}$ and $\Delta P_Q$, $\Delta P_C$ respectively. Typically, a linear interpolation is used but other interpolations can be used.

Furthermore, Q and $\Delta P_Q$ are often linearly related due to the linear flow response in the linear response device, that is: Q is proportional to $\Delta P_Q$. Thus, in some embodiments of the invention, only one of Q and $\Delta P_Q$ is measured during establishment of the characterisation and the other determined from a functional relations ship between the two parameters. In these situations, the corresponding data sets $$(Q, C_{sugar})_{1 \ldots m} <->(\Delta P_Q, \Delta P_C)_{1 \ldots m}$$

may degenerate into $$(C_{sugar})_{1 \ldots m} <->(\Delta P_Q, \Delta P_C)_{1 \ldots m}$$

or $$(Q, C_{sugar})_{1 \ldots m} <->(\Delta P_C)_{1 \ldots m}$$

which may be used as the characterization.

Although embodiments as above have proven to provide advantageous results in determining e.g. sugar concentration, other embodiments may be more effective in measuring on fluids. The above embodiment has a tendency to operate in the low shear viscosity range and in other applications of the invention, a device designed to and operating in high shear viscosity range has proven more effective to provide accurate measurements.

High Shear Viscosity Device

As a result of working with Non-Newtonian fluids, the viscosity depends directly on the local shear. The shear, however, has to exceed a specific value before its effect on the fluid results in a change of the viscosity. This is illustrated in FIG. 3, where the curves μ show that the viscosity is directly related to the local shear rate, for different sugar concentrations in the solution; three curves μ are shown in FIG. 3 each representing a specific sugar concentration.

The curve T represents the threshold in the shear dependence, such that below this, the viscosity stays constant, and this region in shear rate values will be called the "Low shear Newtonian plateau" (LSNP). Above this threshold, the effect of increasing shear either lets the viscosity decrease, where the fluid is then denoted: "shear-thinning", or the viscosity increase, making the fluid be denoted: "shear-thickening".

As seen in FIG. 3, the fluid behavior in the case of sugar solutions becomes shear-thinning.

In order for a fluid measuring device to actively use the shear rate dependence of the viscosity, it has to be secured that the working conditions of the device, both during the final usage, and during the design phase, have to involve shear rates above the LSNP.

The lower right corner of the parameter space in FIG. 3, bounded by the dashed line, marks a region, where the inertial begins to dominate the fluid flow behavior, i.e. the Reynolds number (Re) increases well beyond one.

To prevent mixed effects to influence the fluid property measurements, the fluid measuring device has to utilize the non-linear fluid properties within the shear-thinning region, but avoid dependence on the inertia region, of high Re.

During the design phase of the fluid measuring device, this requirement of sufficiently high shearing was ensured, such that the resulting device actually performs rheological measurements, and in that way broadens the range of applicability covered by the invention.

To distinguish between the two device examples presented, the first device shown in FIG. 1, which is able to measure zero-shear viscosity, will be denoted "Low shear viscosity" device (LSV), while the second device (FIG. 4), to be described in the following, will be denoted "High shear viscosity" device (HSV).

Fluid Property to be Characterized by the HSV Device

As the LSV device (FIG. 1) is able to measure the low shear viscosity of a given fluid, it is preferred to aim towards a second quantity in characterizing these "Generalized Newtonian fluids", and this is the rate of shear-thinning/thickening, which directly corresponds to the slope of the curves in the log-log plot of the shear-thinning region of FIG. 3. The notion "slope" will refer to the local derivative for such curves in log-log plots.

As also seen from FIG. 1, the slope depends on the sugar concentration, so in principle, a similar approach from designing the LSV device i.e. only varying the sugar concentration, could be used in the design process of the HSV device. On the other hand, the aim with the HSV device is to characterize the slope of all different kinds of fluids, and therefore the procedure involves fluid property variations other than changing the sugar concentration.

Design Procedure

In the case of the HSV device, the slope dependence will be implemented directly into the design process by artificially varying the slope of the shear-thinning rate. Closely related to the design process for the LSV device, the HSV design process will first involve a topology optimization of the device to maximize the variation in the pressure difference between two "sidelets" 11a and 11b in FIG. 4 (which are the two closed channel branches at the top and bottom of the device) in order to distinguish the difference between a reference sugar solution, and a fictitious fluid, where the shear-thinning rate has been artificially reduced by a factor F(1-n) compared to the slope of the reference fluid.

When expressed mathematically, and using the same solvent (in this case water), the slope of the reference sugar solution $A_s$ only depends on the sugar concentration $C_s$ in the shear-thinning region: $A_s(C_s)$. Then for the fictitious fluid, the artificial slope $A_f$ is set to: $A_f = F_{(1-n)} A_s(C_s)$, where the factor F is assumed to be within the unit interval, so as to reduce the shear-thinning effect. The index (1-n) in the factor refers to the notation of the slope for a standard Power-law fluid, modeled by the Ostwald-de Waele relationship.

Figure 4:
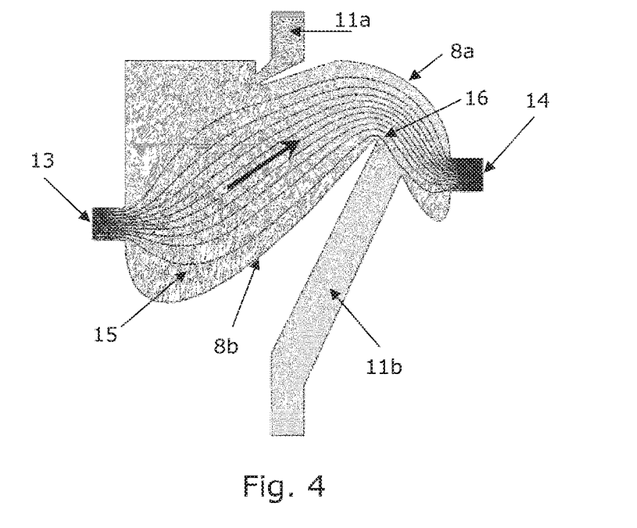
FIG. 4 is a schematic illustration of a HSV device according to the present invention, where the fluid flows through the device from left to right, both indicated by the arrow and by the black streamlines. The pressure is showed throughout the device in grey shading, ranging from high pressure in darkest shade to low pressure in lightest shade. One type of fluid property is characterized by measuring the pressure difference between the two sidelets, which are the two (closed) channel branches at the top and bottom of the device. The device of FIG. 4 is typically used with a capillary device of FIG. 1 or 9. For the results presented herein with device of FIG. 4, the device of FIG. 4 is combined with the capillary device of FIG. 1 to form a measuring device.

From the resulting free-form optimization geometries, the essential active structure is extracted, and the final design is adjusted by a shape optimization process, arriving at the HSV design shown in FIG. 4. Only the fluid region is showed, since the surrounding white void should be filled with a rigid solid material—or the fluid region provided in a solid material. The fluid flows from left to right, as emphasized by streamlines and an arrow, and the pressure is visualized throughout the device by grey shading.

The channel structure of the device, showed in FIG. 4 is characterized by having a single connected transition channel 15 reaching from the inlet 13 to the outlet 14. The upper sidelet 11a is connected to the part of transition channel 15 close to the inlet 13, and the lower sidelet 11b is connected to the transition channel closer to the outlet 14, but not in direct connection to the outlet 14. The main geometrical feature of the transition channel consists of two curved walls 8a, 8b on opposite sides of the channel 15, which acts to deflect the fluid flow into a curved path. The curved wall 8b is shaped so as to define a bump 16.

Figure 5:
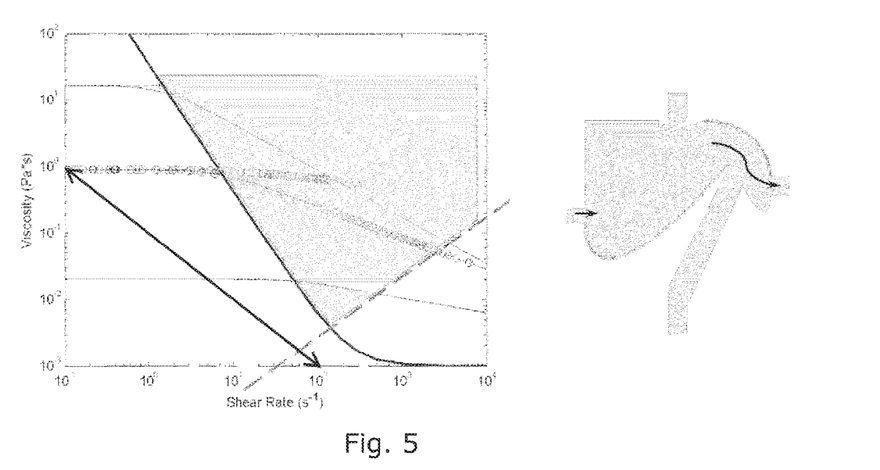
FIG. 5 is a combined illustration that supports that the device characterizes the rheological properties of the fluid.

As illustrated in FIG. 4, the curved wall section 8a defining a bump 16 extends from the inlet 13 of the non-linear response device and to the top of the bump in a convex manner and in a convex manner from the top of the bump 14 and to the outlet 14 of the non-linear response device. The opposing wall section 8b extends from the inlet 13 and to the outlet 14 of the non-linear response device in a concave manner. The opening of one of the sidelets 11b is arranged immediately downstream of maximum height of the bump and the opening of the other sidelet 11a is arranged in a downstream region as depicted in FIG. 4. A result of the two opposite curved wall sections 8a, 8b extending asymmetrically to each other at least through out a part of the flow channel, wherein one of the opposing curved wall sections 8b defines a bump 16 in the flow channel, is a deflection of fluid into a flow pattern with curved stream lines from an inlet and to an outlet of the flow channel with increased shear in flow regions at the bump, as also shown in FIG. 5.

In use, the device of FIG. 4 is typically used with a capillary device of FIG. 1 or FIG. 9.

Fluid Dynamic Principle Employed by the HSV Device

Contrary to the LSV device (FIG. 1), which utilized the inertial effect for characterizing the fluid, regardless of the properties at the shear thinning region, the HSV device is designed to enforce strong shear rates in the fluid, and it does so by deflecting the fluid path by two curved walls 8a and 8b placed at opposite positions of the main transition channel 15 (see FIG. 4).

To underline the contribution from these two walls 8a, 8b, which are located by series of symbols in FIG. 5 right hand side, the local shear rate along these walls are showed by similar symbols in the shear-viscosity plot FIG. 5 left hand side, which is similar to the plot in FIG. 3. The shear-thinning region in the plot has been emphasized by a gray transparent area, and since a substantial part of the shear measurements (symbols) lies within the area, the HSV device indeed functions at shear-thinning conditions, as anticipated.

As a result, different fluids with different shear-thinning rates (slopes) alter the pressure distribution within the HSV device, which can then be measured by the changes in the pressure difference across the sidelets.

Measurement Procedure in Relation to the HSV Device

Similarly to the measurement procedure for the LSV device (FIG. 1), the HSV device (FIG. 4) characterizes fluid properties by comparing the pressure difference across the sidelets on both the HSV device itself (as disclosed in connection with FIG. 1), denoted "$\Delta P_s$-$F_{(1-n)}$", and a capillary device 2 "$\Delta P_s$-Capil." The capillary device 2 is embodied and connected to the HSV device as disclosed in relation to FIG. 2.

Collectively, these two measurements contain sufficient information to measure the slope in the shear-thinning region, even in cases of varying overall flowrates, that is, in situations where the overall flowrate through the device varies in an uncontrolled manner during the measurement.

Figure 6:
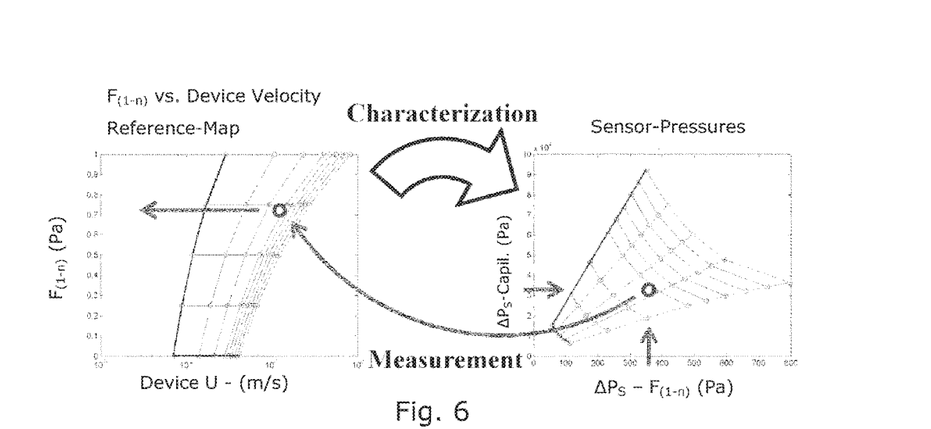
FIG. 6 is an illustration of the procedure for characterizing fluid properties using the HSV device in combination with the capillary device being common to both the LSV and the HSV device. To the left is showed the reference distribution of characterization measurements. The grid at the left plot is then, in the right plot, mapped onto the measurement-space, spanned by the measured pressure differences from the HSV device and the capillary device, and the arrows indicate the procedure for characterizing the fluid from given measurements.

The measurement procedure is illustrated in FIG. 6, which shows both the initial mapping for calibration and an example of a reversed mapping during a measurement.

To the left of FIG. 6 is shown the reference distribution of characterization measurements, where distinct measurements (circles) have been positioned according to their mean velocity and the fluid property factor $F_{(1-n)}$. The grid at the left plot is then mapped onto the measurement-space in the right plot, spanned by the measured pressure differences from the HSV device and the capillary device. In this case, this mapping is the result of multiple numerical simulations of fluid flows through the device. The arrow, from right to left, then indicates the procedure for characterizing the fluid from given measurements. The difference when compared to the similar mapping of the LSV device (FIGS. 1 and 2) is that the velocity in the left initial plot is not distributed regularly.

It should be stressed, that the above example of device functionality has been specifically chosen to characterize the rate of shear-thinning, as this fluid property is generally seen in many fluids and is very illustrative in order to present the functionality of the invention. The invention is not limited to only characterize such simple properties of fluids, as it can be designed to monitor variations of more specialized fluid properties, such that the device may fulfill a specific goal as part of a larger fluid handling facility.

Figure 10:
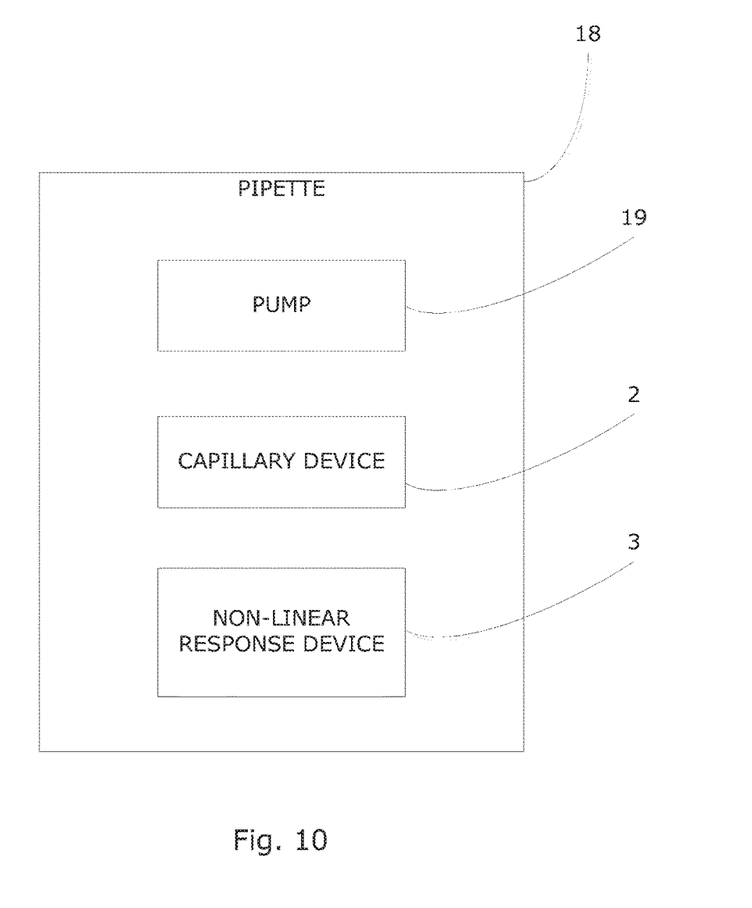
FIG. 10 shows a pipette having a capillary device and a non-linear response device in accordance with an embodiment of the present invention.

A particular preferred embodiment of a device according to the present invention relates to a small handheld device. The device comprises a capillary device 2 and a non-linear response device 3 as outlined above. The device is formed as a pipette 18 with the capillary and the non-linear response device integrated in the pipette, as shown in FIG. 10. The pressure sensors are connected to the a processor either being an integrated part of the pipette or through wires to e.g. a computer. The integrated processor or the computer being equipped with software and a characterisation thereby enabling the processor or the computer to determine the fluid property aimed at. Once activated, the pipette will such fluid through the device and the processor or the computer will provide the magnitude of the fluid property in question. This embodiment furthermore illustrates the advantageous feature of the invention that the flow through the device needs not to be stationary; the flow through the pipette device varies over time but the device is able to provide the desired magnitude of the fluid property in question. The pipette 18 can further include a pump 19.

In a further embodiment, the device is integrated in fluid connection of either a lab equipment, such as a test facility, or a production facility in which a certain fluid property is to be monitored. Again, the pressure sensors are connected to processor means, such as a computer, with software.
Details of the Geometri of the Non-Linear Response Devices Shown in FIGS. 1 and 4

Figure 7:
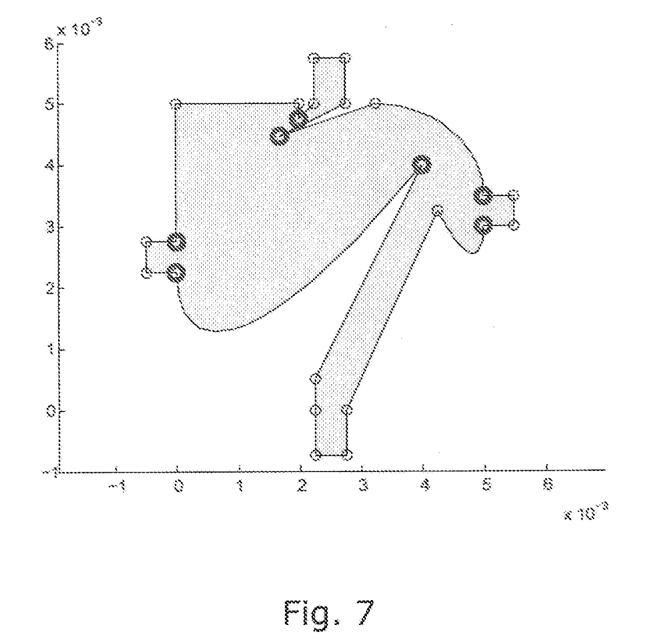
Figure 8:
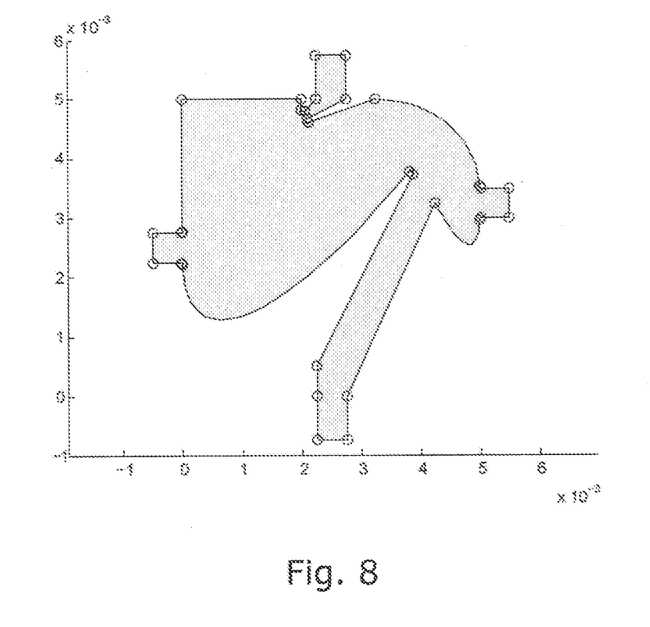
FIG. 8 is an illustration of the second and last step in the procedure for precisely describing the embodiment of the HSV device. It shows the final channel wall geometry of an embodiment of the HSV device arising from fillet procedure described in relation to FIG. 7.

The following table I and II provides details as to the embodiments of the non-linear flow device disclosed in FIG. 1 (table I) and in FIG. 4 (table II). The numerical numbers presented in FIGS. 7 and 8 are in meters; the x-direction is horizontal, the y-direction is vertical.

| X-coordinate | Y-coordinate |
|---|---|
| −1.5000000e−003 | 2.2500000e−003 |
| −1.5000000e−003 | 2.7500000e−003 |
| 0.0000000e+000 | 2.2500000e−003 |
| 0.0000000e+000 | 2.4823456e−003 |
| 0.0000000e+000 | 2.7500000e−003 |
| 1.0000000e−005 | 2.4823456e−003 |
| 7.5000000e−005 | 1.7500000e−003 |
| 7.5000000e−005 | 2.3323456e−003 |
| 2.0000000e−004 | 2.4505824e−003 |
| 2.1000000e−004 | 2.4605824e−003 |
| 2.2500000e−003 | −7.5000000e−004 |
| 2.2500000e−003 | 0.0000000e+000 |
| 2.2500000e−003 | 4.5000000e−003 |
| 2.2500000e−003 | 5.7500000e−003 |
| 2.7500000e−003 | −7.5000000e−004 |
| 2.7500000e−003 | 5.0000000e−004 |
| 2.7500000e−003 | 5.0000000e−003 |
| 2.7500000e−003 | 5.7500000e−003 |
| 4.2000000e−003 | 4.5000000e−003 |
| 4.5000000e−003 | 5.0000000e−004 |
| 5.0000000e−003 | 5.0000000e−004 |
| 5.0000000e−003 | 1.7500000e−003 |
| 5.0000000e−003 | 2.2500000e−003 |
| 5.0000000e−003 | 5.0000000e−003 |
| 6.5000000e−003 | 1.7500000e−003 |
| 6.5000000e−003 | 2.2500000e−003 |

Table I—X and Y Coordinates for the Geometry Disclosed in FIG. 1. The Coordinates are Connected by Straight Lines to Define the Geometry.

The description of the geometry of the device of FIG. 4 is made by chained Bezier curves elements presented in Table II below. Each curve-element is initiated by the text "curve2" in table II, and within a parenthesis follows three vectors consisting of: x-coordinates of the curve control points, y-coordinates of the curve control points, and the weights related to the given Bezier-curve. The number of control points in each curve-element determines the order of the given Bezier-curve.

In the resulting geometry, specific corners are rounded using a "Fillet procedure" (where a circle of given radii has to tangentially touch each of the curve-elements approaching the corner). In the present geometry, the radii of all fillets is constant, equal 3e−5 meter, and the specific corners are indicated by bolded circles in FIG. 7. The final geometry is showed in FIG. 8.

curve2([0.0022500000000000003,
0.0022500000000000003],[0,−7.5e−4],[1,1]),
curve2([0.0022500000000000003,0.00275],[−7.5e−4,−7.5e−4],[1,1]),
curve2([0.00275,0.00275],[−7.5e−4,0],[1,1]),
curve2([0.00275,0.00425],[0,0.00399999−7.5e−4],[1,1]),
curve2([0.00425,0.0050,0.0050],[0.00399999−7.5e−4, 0.00175,0.0030],[1,0.7071067811865475,1]),
curve2([0.0050,0.0055],[0.0030,0.0030],[1,1]),
curve2([0.0055,0.0055],[0.0030,0.0035],[1,1]),
curve2([0.0055,0.0050],[0.0035,0.0035],[1,1]),
curve2([0.0050,0.0050,0.0032500000000000003],[0.0035, 0.0050,0.0050],[1,0.7 071067811865475,1]),
curve2([0.0032500000000000003,0.0017],[0.0050, 0.00448216],[1,1]),
curve2([0.0017,0.00275],[0.00448216,0.0050],[1,1]),
curve2([0.00275,0.00275],[0.0050,0.00575],[1,1]),
curve2([0.00275,0.0022500000000000003],[0.00575, 0.00575],[1,1]), curve2([0.0022500000000000003, 0.0022500000000000003],[0.00575,0.0050],[1,1]), curve2([0.0022500000000000003,0.0020],[0.0050,0.00475195],[1,1]),
curve2([0.0020,0.0020],[0.00475195,0.0050],[1,1]),
curve2([0.0020,0],[0.0050,0.0050],[1,1]),
curve2([0,0],[0.0050,0.00275],[1,1]),
curve2([0,−5.0e-4],[0.00275,0.00275],[1,1]),
curve2([−5.0e-4,−5.0e-4],[0.00275, 0.0022500000000000003],[1,1]),
curve2([−5.0e-4,0],[0.0022500000000000003, 0.0022500000000000003],[1,1]),
curve2([0,0,0.0040],[0.0022500000000000003,−0.00100000,0.00399999],[1,0.7071067811865475,1]),
curve2([0.0040,0.0022500000000000003],[0.00399999, 5.0e-4],[1,1]),
curve2([0.0022500000000000003, 0.0022500000000000003],[5.0e-4,0],[1,1]) fillet of radii 0.3e-4 at corners indicated with bolded circle.

Table II—Bezier-Curve Elements of the Geometry Disclosed in FIG. 4

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A fluid measuring device comprising a capillary device and a non-linear response device, wherein:
    the capillary device comprises a flow channel of the capillary device for determining the volume flow through the flow channel of the capillary device and two sidelets each comprising a pressure sensor arranged at a distal end of the sidelet, the sidelets being arranged in the capillary device to determine the pressure drop over at least a part of the flow channel of the capillary device, wherein at least a portion of the flow channel of the capillary device comprises a uniform cross-sectional area, and
    the non-linear response device comprises a flow channel of the non-linear response device directly connected to the flow channel of the capillary device, the flow channel of the non-linear response device being a curved channel and comprising sidelets each comprising a pressure sensor arranged at a distal end of the sidelet, the sidelets being arranged to determine a pressure drop over at least a part of the flow channel of the non-linear response device, wherein the curved channel comprises:
        two opposite curved wall sections extending asymmetrically to each other at least through out a part of the flow channel of the non-linear response device, wherein one of the opposing curved wall sections defines a bump in the flow channel of the non-linear response device, so as to provide a fluid deflection into a flow pattern with curved stream lines from an inlet and to an outlet of the flow channel of the non-linear response device with increased shear in flow regions at the bump and
        an opening of one of the sidelets is arranged immediately downstream of a maximum height of the bump.

2. The fluid measuring device according to claim 1, wherein the curved wall section opposing the curved wall section defining a bump extends in a manner increasing or decreasing the cross sectional area of the flow channel of the non-linear response device downstream of the bump.

3. The fluid measuring device according to claim 1, wherein the flow channel of the capillary device is a straight channel.

4. The fluid measuring device according to claim 1, wherein
    the curved wall section defining a bump extends from the inlet of the non-linear response device and to the top of the bump in a convex manner and in a convex manner from the top of the bump and to the outlet of the non-linear response device, and
    the opposing wall section extends from the inlet to the outlet of the non-linear response device in a concave manner.

5. The fluid measuring device according to claim 1, wherein the sidelets of the non-linear response device are arranged on opposite sides of the flow channel of the non-linear response device.

6. The fluid measuring device according to claim 1, wherein at least a portion of the flow channel of the capillary device extends symmetrically along a straight line.

7. The fluid measuring device according to claim 1, wherein the volume of the flow channel of the non-linear response device is at least two times larger than the volume of the flow channel of the capillary device.

8. The fluid measuring device according to claim 1, wherein the flow channel of the capillary device, the flow channel of the non-linear response device, and the sidelets of the fluid measuring device are square-shaped.

9. The fluid measuring device according to claim 1, wherein the flow channel of the capillary device, the flow channel of the non-linear response device, and sidelets of the fluid measuring device are provided in a single block of material.

10. The fluid measuring device according to claim 1, wherein the flow channel of the capillary device, the flow channel of the non-linear response device, and sidelets of the fluid measuring device are defined by wall elements made of plastic or metal.

11. The fluid measuring device according to claim 1, wherein the flow channel of the capillary device comprises a narrowing section upstream and an expanding section downstream of a contraction with the sidelets being arranged upstream and downstream of the contraction.

12. The fluid measuring device according to claim 1, wherein the flow channel of the non-linear response device comprises a constriction at an inlet of the flow channel of the non-linear response device, and wherein flow channel of the non-linear response device downstream of the constriction has diverging sides, the diverging sides terminating at a wall having an outlet, a sidelet is arranged at the constriction and a sidelet is arranged at the wall.

13. The fluid measuring device according to claim 1, wherein the flow channel of the non-linear response device comprises a single connected transition channel reaching from an inlet to an outlet, and one of the sidelets is connected to the part of transition channel in vicinity of the inlet, and the other of the sidelets is connected to the transition channel in vicinity of outlet, but not in direct connection with the outlet.

14. The fluid measuring device according to claim 13, wherein a geometrical feature of the transition channel consists of two curved walls on opposite sides of the transition channel, which acts to deflect the fluid flow into a curved path.

15. The fluid measuring device according to claim 1, further comprising a pump for pumping fluid through the capillary device and the non-linear response device.

16. The fluid measuring device according to claim 15, wherein the pump is a manually actuated pump.

17. The fluid measuring device according to claim 15, wherein the measuring device and the pump is formed as a handheld device in the form of a pipette.

18. The fluid measuring device according to claim 1, wherein the measuring device is integrated in lab equipment or a production facility.

19. A method of determining one or more properties of a fluid, the method comprising:
providing a fluid measuring device according to claim 1, and
characterizing an interaction between a given fluid and the flow channel of the capillary device and the flow channel of the non-linear response device, wherein the characterization comprises a determination of:
the values of a property of the fluid,
the values of pressure differences between the sidelets of the non-linear response device, or
the values of either pressure differences between the sidelets of the capillary device, flow rates through the capillary device or both, wherein the method further comprises:
feeding a non-Newtonian fluid through the fluid measuring device at a flow rate producing shear-thinning at least locally in the non-linear response device,
determining the pressure difference between the sidelets of capillary device and of the non-linear response device, and
deriving from the characterization the property of the fluid being fed through the fluid measuring device based on the determined pressure difference between the sidelets of the non-linear device together with the pressure difference between the sidelets of the capillary device.

20. The method according to claim 19, wherein the non-Newtonian fluid is a visco-elastic fluid.

21. The method according to claim 19, wherein the fluid is sugar dissolved in water and the property being determined is the sugar concentration.

22. The method according to claim 19, wherein the fluid is a paint and the property being determined is the rate of shear-thinning.

23. The method according to claim 19, wherein the fluid is an enamel and the property being determined is the rate of shear-thinning.

24. The method according to claim 19, wherein the fluid is an engine oil and the property being determined is the degradation of the oil.

25. The method according to claim 19, wherein the fluid is an engine fuel and the property being determined is the type of engine fuel.

26. The method according to claim 19, further comprising determining the flow rate through the fluid measuring device based on the characterization and the determined pressure differences.

27. The method according to claim 19, further comprising obtaining a characterization by:
feeding a non-Newtonian fluid at number of different known flow rates and with a number of different known properties of the fluid through the fluid measuring device,
recording the pressure differences between the sidelets of the capillary device and the non-linear response device resulting therefrom thereby obtaining a characterization comprising corresponding data sets of:
values of flow rates through the fluid measuring device and property of the fluid, and
pressure differences between the sidelets of the capillary device and the non-linear response device for a number of different volume flow rates through the fluid measuring device and for a number of known and different properties of the fluid.

28. The method according to claim 19, wherein the number of different known flow rates is selected between 50 and 100 and the number of different known properties of the fluid is selected between 50 and 100, whereby the number of corresponding data sets is between 2,500 and 10,000.

29. The method according to claim 19, wherein the corresponding data sets are degenerated into corresponding data sets
of property of the fluid corresponding to the pressure differences between the sidelets of the capillary device and the non-linear response device, or
of values of the flow rate through the fluid measuring device and property of the fluid corresponding to the pressure differences between the sidelets the non-linear response device,
by use of a functional relationship between the flow rate and the pressure between the sidelets of the capillary device.

30. The method according to claim 19, wherein the feeding flow rate of the non-Newtonian fluid through the fluid measuring device at a flow rate producing shear-thinning at least locally in the non-linear response device is constant during the determination of the one or more properties of the fluid.

31. The method according to claim 19, wherein the feeding flow rate of the non-Newtonian fluid through the fluid measuring device at a flow rate producing shear-thinning at least locally in the non-linear response device varies during the determination of the one or more fluid properties of the fluid.

32. The method according to claim 19, wherein the characterization is stored as a database in electronic storage medium.

33. The method according to claim 19, wherein execution of the method is assisted by use of a computer.

* * * * *